United States Patent
Scheibel et al.

(10) Patent No.: US 7,468,347 B2
(45) Date of Patent: Dec. 23, 2008

(54) ALKOXYLATED POLYOL CONTAINING BLEACH ACTIVATING TERMINATING FUNCTIONAL GROUPS

(75) Inventors: Jeffrey John Scheibel, Loveland, OH (US); Julie Ann Menkhaus, Cleves, OH (US); George Douglas Hiler, II, Harrison, OH (US); Marc Eric Gustwiller, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/072,147

(22) Filed: Feb. 25, 2008

(65) Prior Publication Data

US 2008/0214426 A1   Sep. 4, 2008

Related U.S. Application Data

(62) Division of application No. 11/050,054, filed on Feb. 3, 2005, now Pat. No. 7,358,220.

(60) Provisional application No. 60/541,736, filed on Feb. 4, 2004.

(51) Int. Cl.
C11D 1/00 (2006.01)
C11D 1/94 (2006.01)
C11D 3/28 (2006.01)

(52) U.S. Cl. ............ 510/314; 510/370; 510/376; 510/500; 510/505; 546/150; 546/165

(58) Field of Classification Search .......... None
See application file for complete search history.

(56) References Cited

U.S. PATENT DOCUMENTS

| 5,371,119 A | 12/1994 | Bohlander et al. |
| 5,561,235 A | 10/1996 | Gosselink et al. |
| 5,710,116 A | 1/1998 | Miracle et al. |

FOREIGN PATENT DOCUMENTS

| WO | WO 01/98388 A1 | 12/2001 |
| WO | WO 03/104199 A1 | 12/2003 |

*Primary Examiner*—Gregory R Del Cotto
(74) *Attorney, Agent, or Firm*—Stephen T. Murphy; Kim W. Zerby

(57) ABSTRACT

A polyol polymeric structure comprising a bleach activating moiety to give benefits in detergent compositions such as bleaching action, soil suspension, increased surfactant availability in the presence of free hardness.

8 Claims, No Drawings

ALKOXYLATED POLYOL CONTAINING BLEACH ACTIVATING TERMINATING FUNCTIONAL GROUPS

CROSS REFERENCE TO RELATED APPLICATION

This application is a divisional of U.S. application Ser. No. 11/050,054, filed Feb. 3, 2005, now U.S. Pat. No. 7,358,220 which claims benefit under 35 U.S.C. § 119(e) to U.S. provisional application No. 60/541736, filed Feb. 4, 2004.

FIELD OF THE INVENTION

The present invention relates to a bleach activating compound having at least one bleach activator moiety to give hydrophilic and/or hydrophobic soil bleaching in cleaning compositions.

BACKGROUND OF THE INVENTION

Generally, bleach activators rapidly lose their effectiveness at solution temperatures of less than 40° C. While new organic catalysts such as 3,4-dihydro-2-[2-(sulfooxy)decyl] isoquinolimium, inner salt have been developed, they can inactivate certain enzymes and tend to be hydrophobic—thus their aqueous solubility is limited. As most laundry and cleaning compositions are formulated in, or intended to be used with water, formulating cleaning products with such catalysts can be problematic.

Formulability of some current bleach activators, which provide cleaning of bleachable soils, into granular and liquid laundry detergents, hard surface cleaners, dish cleaning compositions, continues to challenge detergent formulators. There also exists a need for materials that are relatively easy to manufacture from sustainable and readily available raw materials, which may be broadly tuned to address specific performance requirements. A multifunctional material that provides cleaning via bleaching action, provides soil suspension capacity and gives increased surfactant availability by preventing formation of larger ordered aggregates of anionic surfactant with free hardness during use is also desired. Specific performance requirements include providing cleaning of hydrophobic stains (grease, oil) to hydrophilic stains (clay) associated with outdoor soils as well as bleachable stains such as grass, wine, tea, coffee, and dingy soil generated as body soils or generated by air pollution. There exists then a need to find bleaching agents that are tunable to provide both hydrophilic and or hydrophobic soil bleaching and to do so under concentrations relevant to laundry and other cleaning products used by consumers.

It has now been discovered that incorporation of an organic bleach catalysts into a polymeric structure solves many of these issues providing effective and efficient multifunctional polymeric catalysts. This has been achieved by using a polymeric structure of a sugar based polyols and other polyols as starting materials for attachment of bleach activator structures discussed herein. Bleach activators described herein are containing as a key structural feature a ring structure.

Polyol materials based on sugars such as sucrose or maltose are known as a sustainable and readily available raw material. Ethoxylates of maltitol are known, e.g., CAS 503446-80-8. Other known ethoxylated polyols include: ethoxylated manitol (CAS 53047-01-2), ethoxylated inostol (CAS 503446-79-5), ethoxylated sorbitol (CAS 53694-15-8). Ethoxylates and propoxylates of ethylene glycol and propylene glycol are also known. See U.S. Pat. No. 5,371,119 and WO 01/98388 A1.

SUMMARY OF THE INVENTION

A bleach activating compound characterized by comprising a polyol source, the polyol source comprising at least two hydroxy moieties, at least one of the hydroxy moieties further comprising a alkoxy moiety, the alkoxy moiety is selected from the group consisting of ethoxy, propoxy, butoxy and mixtures thereof; further wherein at least one of the hydroxy moieties further comprise a bleach activating unit having formula (II):

wherein $R_1$ of formula (II) is independently selected from the group consisting of the polyol source, a $C_6$-$C_{20}$ substituted or unsubstituted aryl; a $C_2$-$C_{20}$ substituted or unsubstituted heteroaryl group, and mixtures thereof; $R_2$ of formula (II) is independently selected from the group consisting of the polyol source, a $C_1$-$C_{20}$ substituted or unsubstituted alkyl; $C_2$-$C_{20}$ substituted or unsubstituted alkenyl, and mixtures thereof; $R_3$ of formula (II) is independently selected from the group consisting of the polyol source, hydrogen, a $C_1$-$C_{20}$ substituted or unsubstituted alkyl, $C_2$-$C_{20}$ substituted or unsubstituted alkenyl, a $C_6$-$C_{20}$ substituted or unsubstituted aryl; a $C_2$-$C_{20}$ substituted or unsubstituted heteroaryl moiety and mixtures thereof; $R_4$ of formula (II) is independently selected from the group consisting of the polyol source, a $C_1$-$C_{20}$ substituted or unsubstituted alkyl, a $C_6$-$C_{20}$ substituted or unsubstituted aryl, a $C_2$-$C_{20}$ substituted or unsubstituted heteroaryl group, and mixtures thereof;

Z of formula (II) is selected from an iminium bond, an oxaziridinium bond, or is selected to result in a single bond between the nitrogen and the carbon of formula (II); such that $R_1$, $R_2$, $R_3$ and $R_4$ of formula (II) in combination with the iminium bond, the oxaziridinium bond, or the single bond between the nitrogen and carbon of formula (II), are selected to form at least one ring structure; in that the two moieties from the group of $R_1$, $R_2$, $R_3$ and $R_4$ of formula (II) selected to form the ring structure do not comprise the polyol source.

The present invention also relates to a process of making the bleach activating compound, a cleaning composition comprising the bleach activating compound, and a method of using the cleaning composition.

DETAILED DESCRIPTION OF THE INVENTION

As used herein "substituted" mean one or more $C_1$-$C_{10}$ alkyl moiety, one or more hydroxyl moiety, or any combinations thereof.

Incorporated and included herein, as if expressly written herein, are all ranges of numbers when written in a "from X to Y" or "from about X to about Y" format. It should be understood that every limit given throughout this specification will include every lower or higher limit, as the case may be, as if such lower or higher limit was expressly written herein. Every range given throughout this specification will include every narrower range that falls within such broader range, as if such narrower ranges were all expressly written herein.

Unless otherwise indicated, weight percentage is in reference to weight percentage of the detergent composition. All temperatures, unless otherwise indicated are in Celsius.

Polyol compounds such as sugar based materials and polyethylene/polypropylene glycol materials are sustainable and readily available raw materials that lend themselves to be broadly tuned to address specific formulabiliy and performance requirements. As used herein "tune" means having the ability to manipulate the chemical structure of the polyol compounds to achieve distinguishing chemical functionality. For example, an alkoxylated polyol compound modified by comprising a bleach activator moiety is a tuned structure giving desired characteristics for specific formulability and performance requirements. Another example, an alkoxylated polyol compound modified by comprising a bleach activator moiety and anionic capping unit is a tuned structure giving desired characteristics.

The polyol compounds useful in the present invention comprises at least two hydroxy moieties, preferably more than two hydroxy moieties, more preferably three hydroxy moieties. Most preferably six or more hydroxy moieties. At least one of the hydroxy moieties further comprising an alkoxy moiety, the alkoxy moiety is selected from the group consisting of ethoxy (EO), propoxy (PO), butoxy (BO) and mixtures thereof preferably ethoxy and propoxy moieties, more preferably ethoxy and propoxy moieties. The average degree of alkoxylation is from about 0 to about 200, from about 0.1 to about 200, preferably from about 4 to about 80, more preferably from about 10 to about 50. Alkoxylation is preferably block alkoxylation.

The polyol compounds useful in the present invention further have at least one of the hydroxy moieties comprising at least one bleach activator unit. Further modifications or tuning of the compound may occur, but one bleach activator moiety must be present in the compound of the present invention. One embodiment comprises more than one hydroxy moiety further comprising an alkoxy moiety terminating in a bleach activator unit. For example formula (I):

Formula (I)

wherein x of formula (II) is from about 0.1 to about 200, preferably from about 40 to about 80; $R_1$, $R_2$, $R_3$, and Z are defined below in formula (II); y of formula (I) is selected from hydrogen, methyl, ethyl, propyl, butyl and mixtures thereof. A used herein, the bleach activator unit has formula (II) below:

wherein $R_1$ of formula (II) is independently selected from the group consisting of the polyol source, a $C_6$-$C_{20}$ substituted or unsubstituted aryl; a $C_2$-$C_{20}$ substituted or unsubstituted heteroaryl group, and mixtures thereof. Preferably, $R_1$ is a $C_6$-$C_{20}$ substituted aryl, wherein the substitution is the polyol source.

$R_2$ of formula (II) is independently selected from the group consisting of the polyol source, a $C_1$-$C_{20}$ substituted or unsubstituted alkyl. $C_6$-$C_{20}$ substituted or unsubstituted alkenyl, and mixtures thereof.

$R_3$ of formula (II) is independently selected from the group consisting of the polyol source, hydrogen, or a $C_1$-$C_{20}$ substituted or unsubstituted alkyl, $C_2$-$C_{20}$ substituted or unsubstituted alkenyl $C_6$-$C_{20}$ substituted or unsubstituted aryl; $C_2$-$C_{20}$ substituted or unsubstituted heteroaryl moiety and mixtures thereof.

$R_4$ of formula (II) is independently selected from the group consisting of the polyol source, a $C_6$-$C_{20}$ substituted or unsubstituted aryl, a $C_2$-$C_{20}$ substituted or unsubstituted heteroaryl group, and mixtures thereof.

In formula (II), at least one of $R_1$, $R_2$, $R_3$ and $R_4$ is a polyol source and wherein at least two of $R_1$, $R_2$, $R_3$ and $R_4$ not selected as a polyol source form a ring structure.

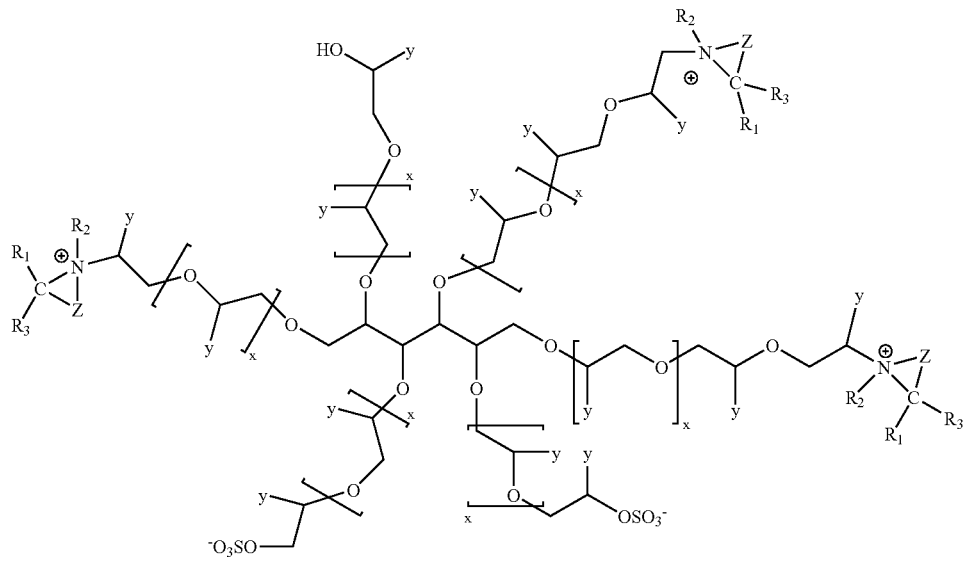

Z of formula (II) is selected from an iminium bond, thereby making a double bond between the nitrogen and carbon of formula (II) or Z is selected from an oxaziridinium bond, thereby having a nitrogen, carbon, and oxygen structure or Z is selected to be such that a single bond exists between the nitrogen and the carbon.

When Z of formula (II) is selected to be an iminium bond, the nitrogen then becomes quaternized or has a positive charge. $R_1$, $R_2$, $R_3$, and $R_4$ of formula (II) are selected such that at least one ring structure results from a selection of two moieties from the group of $R_1$, $R_2$, $R_3$, and $R_4$ of formula (II) in combination with the iminium bond the oxaziridinium bond of formula (II) or the single bond between N=C or formula (II). The two moieties from the group of $R_1$, $R_2$, $R_3$, and $R_4$ of formula (II) selected to form the ring structure would not be selected to comprise the polyol source, or in other words the polyol source would not be directly connected to the iminium bond the oxaziridinium bond or the single bond. However, the polyol source could be used as a substitution group on the ring structure.

Preferably at least one of $R_1$, $R_3$ and $R_4$ of formula (II) is selected to be a substituted or unsubstituted aryl. Ring structures may be saturated or unsaturated (i.e., aromatic). Preferably the rings are at least partially unsaturated. Ring structures may be a single ring or a multiple ring structure; preferably the ring structures are double ring structures.

Substitution of the ring structure may occur with any known type of substitution known to one of skill in the art. Substitution may be carbon, sulfur nitrogen, or oxygen containing. Preferred substitutions, when present, include the polyol source, $C_1$-$C_{20}$ (or appropriate carbon number for suggested group, for example $C_6$-$C_{20}$ phenyl or alkyl phenyl groups) alkyl, alkenyl, alkynyl, alkyldienyl, cycloalkyl, phenyl, alkyl phenyl, naphthyl, anthryl, phenanthryl, fluoryl, steroid groups; oxygen containing substitutions such as hydroxy, acyl or keto, ether, epoxy, carboxy, and ester containing substitutions, preferably —$CH_2OH$, —$CCH_3CH_3OH$, —$CH_2COOH$, —$C(O)$—$(CH_2)_8CH_3$, —$OCH_2CH_3$, =O, —OH, —$CH_2$—O—$CH_2CH_3$, —$CH_2$—O—$(CH_2)_2$—OH, nitrogen containing substitutions such as amino groups, the nitro group, azo groups, ammonium groups, amide groups, azido groups, isocyanate groups, cyano groups and nitrile groups, preferably —$NHCH_3$, —$NH_2$, —$NH_3^+$, —$NO_2$, sulfur containing substitutions such as sulfur-containing acids and acid ester groups, thioether groups, mercapto groups and thioketo groups, preferably —$SCH_2CH_3$, —$CH_2S(CH_2)_4CH_3$, —$SO_3CH_2CH_3$, $SO_2CH_2CH_3$, —$CH_2COSH$, —SH, —$CH_2SCO$, —$CH_2C(S)CH_2CH_3$, —$SO_3H$. In one embodiment, the bleach activating unit has the formula (II) above, wherein Z of formula (II) is an iminium bond to result in formula (III):

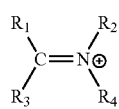
(III)

wherein $R_1$, $R_2$, $R_3$ and $R_4$ of formula (III) are as defined in formula (II) above. R, $R_1$, $R_2$, $R_3$ and $R_4$ of formula (III) are selected such that at least one ring structure results from a selection of two moieties from the group of $R_1$, $R_2$, $R_3$ and $R_4$ of formula (III) in combination with the iminium bond of formula (III). The two moieties from the group of $R_1$, $R_2$, $R_3$, and $R_4$ of formula (II) selected to form the ring structure would not be selected to comprise the polyol source, or in other words the polyol source would not be directly connected to the iminium bond of formula (III). However, the polyol source could be used as a $C_6$-$C_{20}$ substitution group on the ring structure. Preferably at least one of $R_1$, $R_3$ and $R_4$ of formula (II) is selected to be a substituted or unsubstituted aryl. Ring structures may be saturated or unsaturated (i.e., aromatic). Preferably the rings are at least partially unsaturated. Ring structures may be a single ring or a multiple ring structure, preferably the ring structures are double ring structures.

Substitution of the ring structure may occur with any known type of substitution known to one of skill in the art as described above for formula (II).

Nonlimiting Example of Possible Ring Structures for Formula (III) Include:

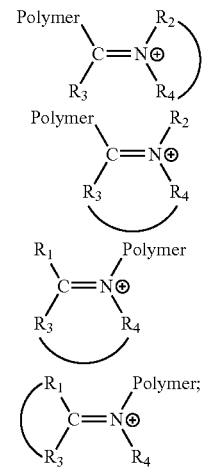

wherein the curved line connected two moieties represents a ring structure and "polymer" represents the polyol source. In another embodiment, $R_1$, $R_3$ and $R_4$ are selected to result in formula (IV) and $R_2$ is selected to be the polyol source.

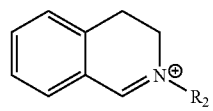
formula (IV)

In one embodiment, the bleach activating unit has the formula (II) above, wherein Z of formula (II) is an oxaziridinium bondto result in formula (IV) below:

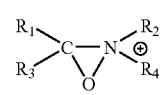
(IV)

wherein $R_1$ $R_2$, $R_3$ and $R_4$ of formula (IV) are as defined in formula (II) above. R, $R_1$, $R_2$, $R_3$ and $R_4$ of formula (IV) are selected such that at least one ring structure results from a selection of two moieties from the group of $R_1$, $R_2$, $R_3$ and $R_4$ of formula (IV) in combination with the oxaziridinium bond of formula (IV). The two moieties from the group of $R_1$, $R_2$, $R_3$, and $R_4$ of formula (II) selected to form the ring structure would not be selected to comprise the polyol source, or in other words the polyol source would not be directly connected to the oxaziridinium bond. However, the polyol source could be used as a substitution group on the ring structure. Preferably at least one of $R_1$, $R_3$ and $R_4$ of formula (II) is selected to be a $C_6$-$C_{20}$ substituted or unsubstituted aryl. Ring structures may be saturated or unsaturated (i.e., aromatic).

Preferably the rings are at least partially unsaturated. Ring structures may be a single ring or a multiple ring structure, preferably the ring structures are double ring structures.

Substitution of the ring structure may occur with any known type of substitution known to one of skill in the art as described above for formula (II). None limiting example of possible ring structures for formula (IV) include:

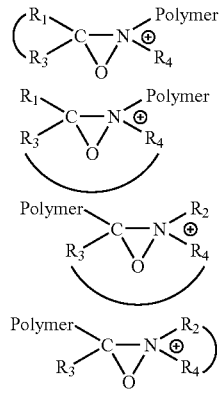

wherein the curved line connected two moieties represents a ring structure and "polymer" represents the polyol source.

In one embodiment, the bleach activating unit has the formula (II) above, wherein Z of formula (II) is selected to result in a single bond between the nitrogen and the carbon to result in formula (V) below:

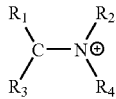

(V)

wherein $R_1$, $R_2$, $R_3$ and $R_4$ of formula (V) are as defined in formula (II) above. $R_1$, $R_2$, $R_3$ and $R_4$ of formula (V) are selected such that at least one ring structure results from a selection of two moieties from the group of $R_1$, $R_2$, $R_3$ and $R_4$ of formula (V) in combination with the single bond between the nitrogen and the carbon of formula (V). The two moieties from the group of $R_1$, $R_2$, $R_3$, and $R_4$ of formula (II) selected to form the ring structure would not be selected to comprise the polyol source, or in otherwords the polyol source would not be directly connected to the single bond between the nitrogen and the carbon of formula (V). However, the polyol source could be used as a $C_6$-$C_{20}$ substitution group on the ring structure. Preferably at least one of $R_1$, $R_3$ and $R_4$ of formula (V) is selected to be a substituted or unsubstituted aryl. Ring structures may be saturated or unsaturated (i.e., aromatic). Preferably the rings are at least partially unsaturated. Ring structures may be a single ring or a multiple ring structure; preferably the ring structures are double ring structures.

Substitution of the ring structure may occur with any known type of substitution known to one of skill in the art as described above for formula (II).

Nonlimiting Example of Possible Ring Structures for Formula (V) Include:

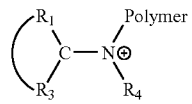

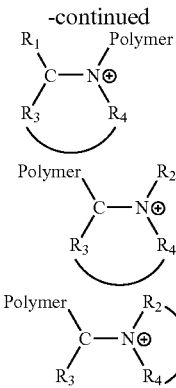

wherein the curved line connected two moieties represents a ring structure and "polymer" represents the polyol source. One skilled in the art will recognize that formula (V) may be protonated, as shown, or may be nonprotonated.

Suitable polyol compounds for starting materials for use in the present invention include maltitol, sucrose, xylitol, glycerol, pentaerythitol, glucose, maltose, matotriose, maltodextrin, maltopentose, maltohexose, isomaltulose, sorbitol, poly vinyl alcohol, partially hydrolyzed polyvinylacetate, xylan reduced maltotriose, reduced maltodextrins, polyethylene glycol, polypropylene glycol, polyglycerol, diglycerol ether and mixtures thereof. Preferably the polyol compound is sorbitol, maltitol, sucrose, xylan, polyethylene glycol, polypropylene glycol and mixtures thereof. Preferably sorbitol, maltitol, sucrose, xylan, and mixtures thereof.

Suitable anionic capping unit include sulfate, sulfosuccinate, succinate, maleate, phosphate, phthalate, sulfocarboxylate, sulfodicarboxylate, propanesultone, 1,2-disulfopropanol, sulfopropylamine, sulphonate, monocarboxylate, methylene carboxylate, ethylene carboxylate, carbonates, mellitic, pyromellitic, sulfophenol, sulfocatechol, disulfocatechol, tartrate, citrate, acrylate, methacrylate, poly acrylate, poly acrylate-maleate copolymer, and mixtures thereof. Preferably the anionic capping units are sulfate, sulfosuccinate, succinate, maleate, sulfonate, methylene carboxylate and ethylene carboxylate.

Tuning of the polyol compounds can be derived from one or more modifications, dependant upon the desired formulability and performance requirements. Tuning can include incorporating an anionic, cationic, or zwitterionic charge modifications to the polyol compounds.

Process of Making

The present invention also relates to a process for making the compound of the present invention. In one embodiment the process for making the compound of the present invention comprises the steps of:

(a) optional alkoxylating a polyol source comprising at least two hydroxy moieties to form an alkoxylated polyol having an average degree of alkoxylation between about 0 and about 200; preferably between about 0.1 and about 200; preferably from about 4 to about 80; more preferably from about 10 to about 50; to form an alkoxylated polyol comprising at least one alkoxy moiety. Alternatively, an alkoxylated polyol, such as CAS 52625-13-5, a propoxylated sorbitol or sorbitol polyoxy ethylene ether available from Lipo Chemicals Inc., may be used as the starting material of the present invention. If the average degree of alkoxylation is not a desired level, an alkoxylation step may be used to achieve the desired degree of alkoxylation from 0 to about 200, preferably between about 0.1 and about 200; preferably from about 4 to about 80; more preferably from about 10 to about 50.

(b) Reacting at least one hydroxy moiety of the compound with an anionic capping unit to form an anionic polyol. Preferably more than one hydroxy moiety of the compound is reacted with an anionic capping unit. Preferable anionic capping unit include sulfate, phosphate, carbonate, and mixtures thereof. More preferably the anionic capping units are sulfate.

(c) Should the optional step (a) be utilized, reacting at least one resulting terminal hydroxy group of the alkoxy moiety with an anionic capping unit to form an anionic alkoxylated polyol.

(d) Substituting the anionic capping unit of the anionic polyol and/or the anionic alkoxylated polyol with an excess of the bleach activating unit of formula (II) wherein Z of formula (II) is selected to result in a single bond between the nitrogen and carbon, and $R_4$ of formula (II) is selected as a hydrogen, forming an amine terminating polyol and/or amine terminating alkoxylated polyol. The amine terminating polyol and/or amine terminating alkoxylated polyol is a functional polymer in and of itself and is a precursor to a bleach activator compound comprising a bleach activator unit by the next step (e) below.

(e) Oxidizing the amine terminated polyol and/or amine terminated alkoxylated polyol to convert the bleach activating unit of formula (II) wherein Z of formula (II) is a single bond between the nitrogen and the carbon of formula (II) to result in the iminium bond of formula (II) forming a bleach activator compound comprising a bleach activator unit. The oxaziridinium ring containing version of the present invention may be produced by contacting an iminium ring containing version of the present invention with an oxygen transfer agent such as a peroxycarboxylic acid. Such species can be formed in situ and used without purification.

A nonlimiting synthesis scheme is exemplified in Synthesis Scheme I below.

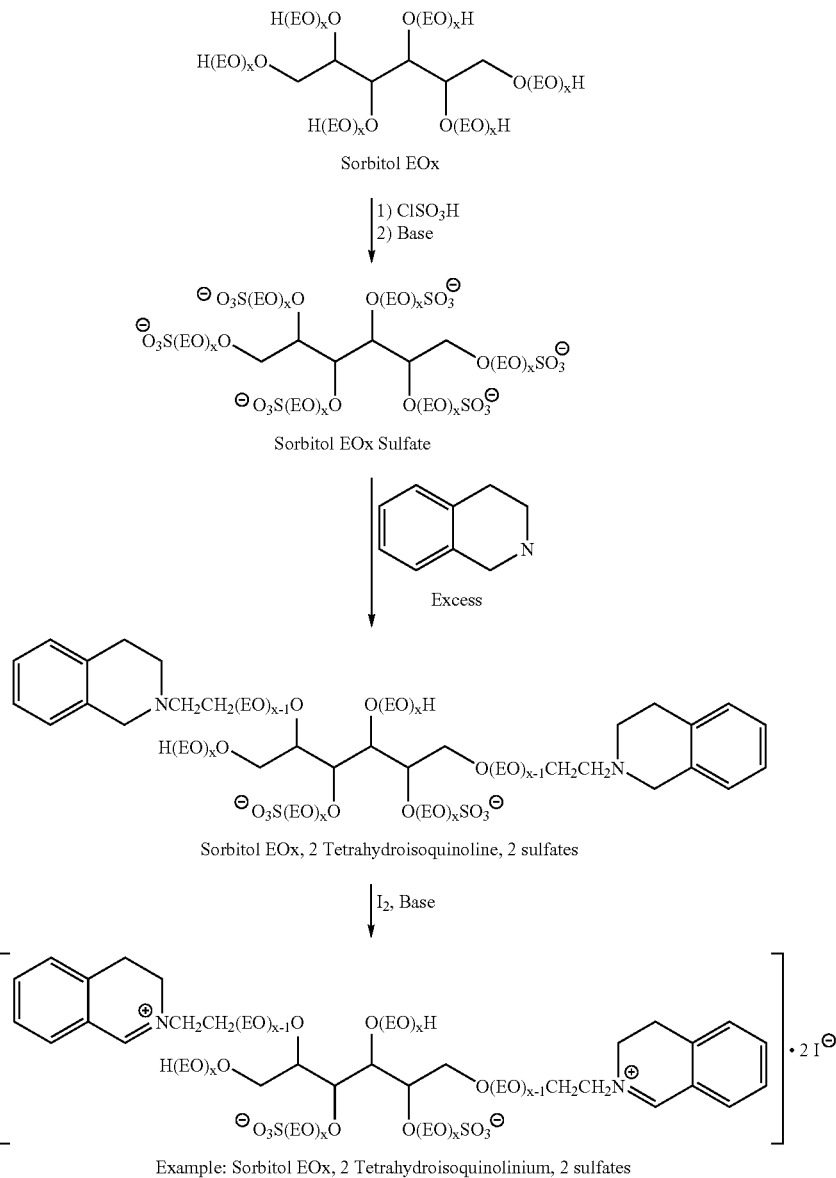

Synthesis Scheme II:

In another embodiment, the process for making the compound of the present invention comprises the steps of:

(a) alkoxylating a polyol source comprising at least two hydroxy moieties to form an alkoxylated polyol having an average degree of alkoxylation between about 0 and about 200; preferably between about 0.1 and about 200; preferably from about 4 to about 80; more preferably from about 10 to about 50; to form an alkoxylated polyol comprising at least one alkoxy moiety. Alternatively, an alkoxylated polyol, such as CAS 52625-13-5, a propoxylated sorbitol or sorbitol polyoxy ethylene ether available from Lipo Chemicals Inc., may be used as the starting material of the present invention. If the average degree of alkoxylation is not a desired level, an alkoxylation step may be used to achieve the desired degree of alkoxylation from 0 to about 200, preferably between about 0.1 and about 200; preferably from about 4 to about 80; more preferably from about 10 to about 50.

(b) Reacting at least one hydroxy moiety of the alkoxylated polyol with an olefinic containing reagent to form an olefinically terminated alkoxylated polyol. Preferably more than one hydroxy moiety of the compound is reacted with an olefinic containing reagent. The olefinic containing reagent may be selected such as allyl chloride, allyl bromide, and mixtures thereof.

(c) Alkylating, in the presence of a catalyst, a substituted or unsubstituted aryl of a bleach activating unit of formula (II), with the olefinically terminated alkoxylated polyol, wherein in the bleach activating unit of formula (II) has Z of formula (II) selected to result in a single bond between the nitrogen and carbon and none of $R_1$, $R_2$, $R_3$ and $R_4$ are selected as the polyol source, forming a alkylated polyol wherein at least one terminal hydroxyl group of the alkoxylated polyol is the bleach activating unit of formula (II).

(d) If $R_4$ of formula (II) is hydrogen, then the compound of step (c) is reacted with an alkyl halide forming a tertiary amine of the compound of Scheme II step (c). $R_4$ of formula (II) is now as defined above as being selected from an substituted or unsubstituted aryl, a substituted or unsubstituted heteroaryl group, and mixtures thereof.

(e) Oxidizing the compound of Scheme II step (d) to form the bleach activating unit of formula (II) wherein Z of formula (II) is selected to result in the iminium bond forming a bleach activator compound comprising a bleach activator unit.

The oxaziridinium ring containing version of the present invention may be produced by contacting an iminium ring containing version of the present invention with an oxygen transfer agent such as a peroxycarboxylic acid. Such species can be formed in situ and used without purification.

A Nonlimiting Synthesis Scheme is Exemplified in Synthesis Scheme II Below.

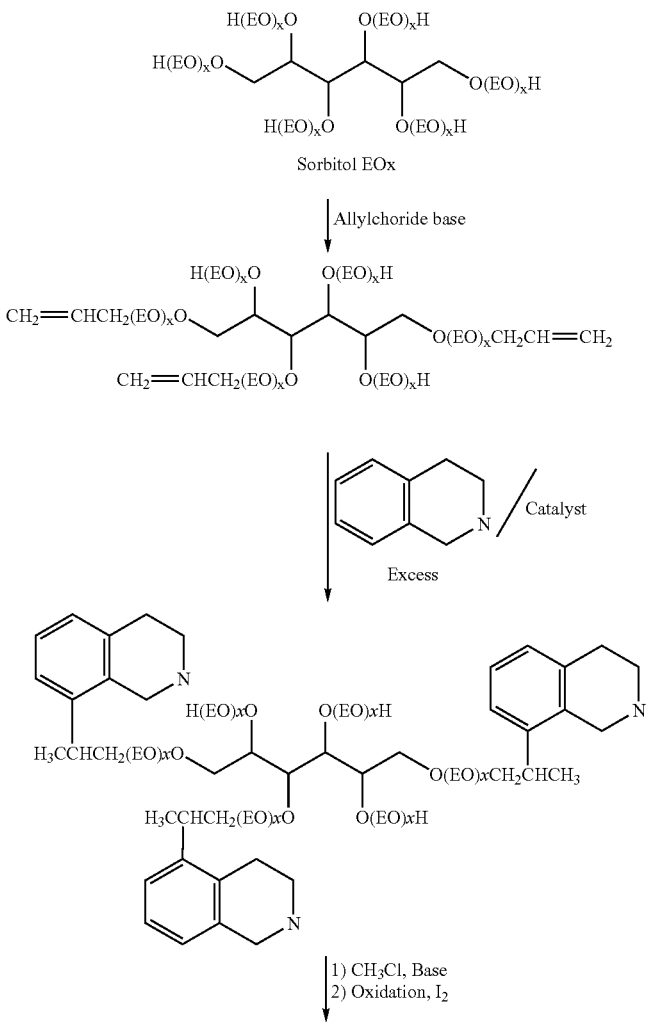

-continued

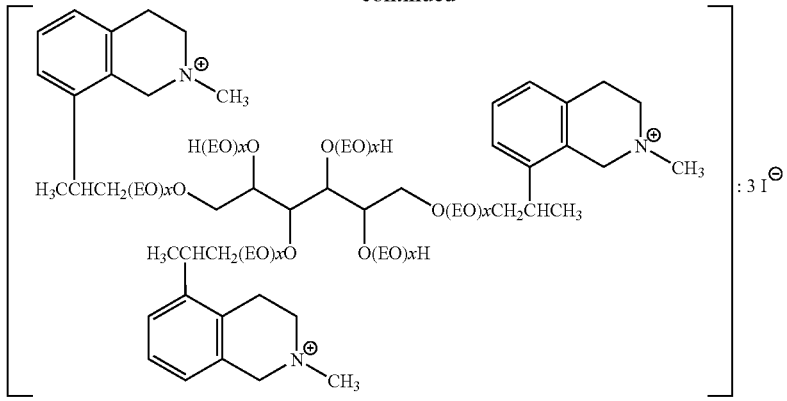

Alternatively to synthesis scheme II, instead of 1,2,3,4-tetrahydroisoquinoline, N-methyl-1,2,3,4 tetrahydroisoquinoline as reactant in step 2 of synthesis scheme II and thus eliminates the reaction step 3 of synthesis scheme II involving methylchoride. All other steps remain the same. Furthermore, the attachment points shown for synthesis scheme II and thus also in the alternative route for the aromatic ring of the substituted or unsubstituted tetrahydroisoquinoline to the alkoxylated polyol is not meant to be limited to the attachment points shown in reaction synthesis scheme II.

Synthesis Scheme III:

In another embodiment, the process for making the compound of the present invention comprises the steps of:

(a) alkoxylating a polyol source comprising at least two hydroxy moieties to form an alkoxylated polyol having an average degree of alkoxylation between 0 and about 200; preferably between about 0.1 and about 200; preferably from about 4 to about 80; more preferably from about 10 to about 50; to form an alkoxylated polyol comprising at least one alkoxy moiety. Alternatively, an alkoxylated polyol, such as CAS 52625-13-5, a propoxylated sorbitol or sorbitol polyoxy ethylene ether available from Lipo Chemicals Inc., may be used as the starting material of the present invention. If the average degree of alkoxylation is not a desired level, an alkoxylation step may be used to achieve the desired degree of alkoxylation from 0 to about 200, preferably between about 0.1 and about 200; preferably from about 4 to about 80; more preferably from about 10 to about 50.

(b) reacting the alkoxylated polyol with a epichlorohydrin in the presence of a Lewis acid catalyst, preferably $SnCl_4$, followed by reaction with a base to form a glycidol ether capped alkoxylated polyol.

(c) reacting the glycidol ether capped alkoxylated polyol with sulfur trioxide to form a cyclic sulfate capped alkoxylated polyol, and the cyclic sulfate capped alkoxylated polyol is then reacted with 3,4-dihydroisoquinoline to form the bleach activating alkoxylated polyol of the present invention. The bleach activating alkoxylated polyol comprises a both an iminium bond (cationic charge) and a sulfo moiety (anionic charge) on the same alkoxylated polyol unit of the bleach activating alkoxylated polyol.

The oxaziridinium ring containing version of the present invention may be produced by contacting an iminium ring containing version of the present invention with an oxygen transfer agent such as a peroxycarboxylic acid. Such species can be formed in situ and used without purification.

A nonlimiting synthesis scheme is exemplified in Synthesis Scheme III below.

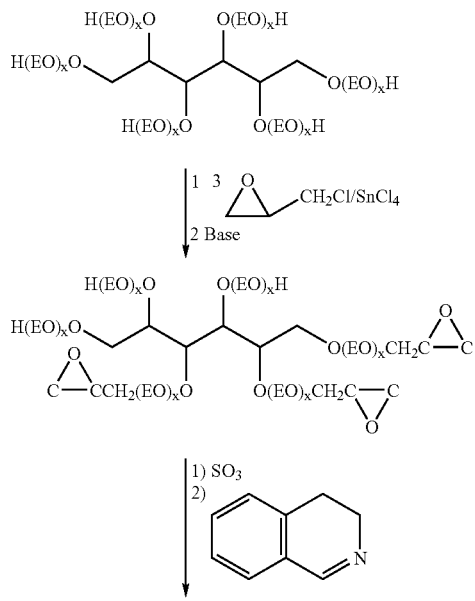

-continued

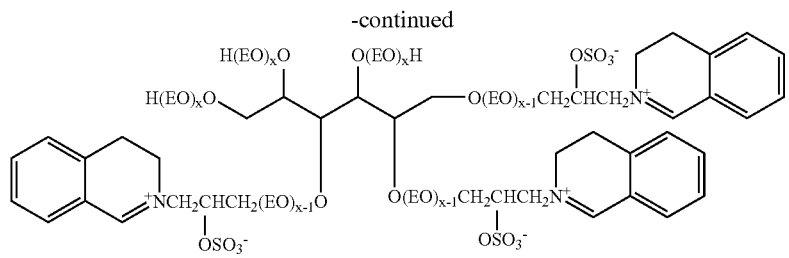

A specific description of the process of the present invention is described in more detail below.

EXAMPLE 1

Synthesis Scheme I

Step 1: Ethoxylation of Polyol

Ethoxylation of the polyol, such as sorbitol, may be completed by any known technique, such as that described in EP 174436 A1 Propoxylation and butoxylation may also be completed by known techniques.

Add sorbitol (17.5 g, 0.0962 mol) to an autoclave, purge the autoclave with nitrogen, heat sorbitol to 110-120° C.; autoclave stirred and apply vacuum to about 67.7 kPa (20 mmHg).

Vacuum is continuously applied while the autoclave is cooled to about 110-120° C. while introducing 6.2 g of a 25% sodium methoxide in methanol solution (0.0288 moles, to achieve a 5% catalyst loading based upon hydroxy moieties). The methanol from the methoxide solution is removed from the autoclave under vacuum. Agitator power and temperature values gradually increase as methanol is removed from the autoclave and the viscosity of the mixture increases and stabilizes in about 1.5 hours indicating that most of the methanol has been removed. The mixture is further heated and agitated under vacuum for an additional 30 minutes.

Vacuum is removed and the autoclave is cooled to or kept at 110° C. while it is being charged with nitrogen to 1725 kPa (250 psia) and then vented to ambient pressure. The autoclave is charged to 1380 kPa (200 psia) with nitrogen. Ethylene oxide is added to the autoclave incrementally while closely monitoring the autoclave pressure, temperature, and ethylene oxide flow rate while maintaining the temperature between 110 and 120° C. and limiting any temperature increases due to reaction exotherm. After the addition of 483 g of ethylene oxide (10.97 mol, resulting in a total of 19 moles of ethylene oxide per mol of OH), the temperature is increased to 120° C. and the mixture stirred for an additional 2 hours.

The reaction mixture is then collected into a 22 L three neck round bottomed flask purged with nitrogen. The strong alkali catalyst is neutralized by slow addition of 2.8 g methanesulfonic acid (0.00288 moles) with heating (110° C.) and mechanical stirring. The reaction mixture is then purged of residual ethylene oxide and deodorized by sparging an inert gas (argon or nitrogen) into the mixture through a gas dispersion frit while agitating and heating the mixture to 120° C. for 1 hour. The final reaction product, approximately 500 g, is cooled slightly, and poured into a glass container purged with nitrogen for storage.

Alternatively, polyol may be purchased with a degree of alkoxylation that is below that desired, such as CAS 52625-13-5, a propoxylated sorbitol or sorbitol polyoxy ethylene ether available from Lipo Chemicals Inc., wherein the desired degree of alkoxylation is achieved by the processes known and/or described above.

Step 2: Sulfation of Sorbitol $EO_{114}$ (Average of 19 EO Moieties Per Hydroxy Moiety)

Weigh into a 500ml Erlenmeyer flask Sorbitol $E_{114}$ (299.7 g, 0.058 mol) and methylene chloride (300 g). Equip the flask with a magnetic stirring bar and stir the material until complete dissolution. Place the flask in an ice bath until the solution reaches about 10° C. Stir vigorous while slowing pouring chlorosulfonic acid (48.3 g, 0.415 mol) over the period of about 5 minutes. Stir the reaction solution in the ice bath for 1.5 hours.

Place a solution of sodium methoxide (197 g of 25% in methanol) in 50 g of methylene chloride in a 1 L Erlenmeyer flask ("base solution") and chill in an ice bath until the temperature of the solution reaches about 10° C. Stir the base solution vigorous using a magnetic stirring bar. Slowly pour the reaction solution into the base solution over a period of about 3 minutes. A mild exotherm should be observed. The solution becomes milky as salts form. After addition is complete, measure the pH to be about 12. Add to this solution about 100 ml of distilled water, and transfer the resulting emulsion to a 1 L round bottom flask and use a rotary evaporator at 50° C. to strip, in portions, to obtain a clear solution. Transfer the solution to a Kulgelrohr apparatus. At 60° C. and 133 Pa (1 mm Hg) strip the solution to yield 366 g of off-white waxy solid, 90% active (10% salts).

Carbon NMR spectrum (500 MHz; pulse sequence: s2pu1, solvent $D_2O$; relax. delay 0.300 sec, pulse 45.0; acq. time 1.090 sec) shows an absence of alcohol groups at about 60 ppm and the emergence of a new peak at about 67 ppm consistent with formation of the end group sulfate. Proton NMR spectrum (500 MHz or 300 MHz; pulse sequence: s2pu1, solvent $D_2O$; relax. delay 1.000 sec, pulse 45.0; acq. time 2.345 sec) shows a new peak at about 4 ppm which was integrated against the ethoxy group protons at about 3.5 ppm and is consistent with the molecule having 6 end group sulfates.

Step 3: Preparation of Activating Amine Terminated Alkoxylated Polyol Containing a Bleach Activator Precursor Weigh into each of three 7-ml high-pressure mini-reactors equipped with magnetic stirring bars sorbitol $EO_{114}$ hexasulfate from step 2 (3.5 g, 0.00406 mol sulfates) and 1,2,3,4-tetrahydroisoquinoline (1.05 g, 0.00812 mol). Equip one mini-reactor with a thermocouple connected to a digital thermometer, and heat the three reactors in a REACI-THERM III® heating/stirring module at about 170° C. for 3 hours. After cooling, combine the reactions and dissolve in about 75 ml methanol. Remove the precipitate by centrifugation. Strip the supernatant on the rotary evaporator at 50° C. Remove the excess amine on a Kugelrohr apparatus at 120° C. at about 133 Pa (1 mm Hg) for 2 hours to afford 7.5 g of brown waxy solid. Proton and carbon NMR indicates about 2.75 tetrahydroisoquinoline groups attached to the polyol source, with about 2 sulfate groups remaining.

Step 4: Oxidizing the Amine Terminated Alkoxylated Polyol to an Iminium Terminated Alkoxylated Zwitterionic Polyol (Bleach Activator of Formula (IV))

Dissolve a 4.0 g sample of the product of Step 3 (~0.0020 mol amine groups) in 30 g methanol and place in a 3-neck 100 ml round bottom flask equipped with a magnetic stirring bar, heating mantle, thermometer and condenser. Add to the flask 0.48 g potassium acetate (0.0049 mol). Heat the solution to reflux. Add dropwise a solution of 1.0 g iodine crystals (0.0039 mol) in 15 g of methanol to the heated solution over about 5 minutes. Heat the mixed solution at reflux overnight (about 17 hours). Remove via filtration a white precipitate formed upon cooling. Strip a small aliquot of the solution for analysis. Proton and carbon NMR indicates a molecule having about 2 imminium sites and about 2 sulfates on average per molecule of the bleach activating compound, with a small amount of isoquinoline type functional groups evident.

Optional Step 5: Ion Exchange of Iodide Counterion from Product of Step 4

It may be desirable depending on the application of the bleach activating compound to remove the iodide from the reaction product via ion exchange. This can be accomplished via many ways by one skilled in the art. One specific ion exchange resin which would be useful is known as IRA400 (R) sold by many various chemical supply houses.

EXAMPLE 2

Synthesis Scheme II

Step 1: Preparation of Allyl Capped Alkoxylated Polyol

Add to a 250 ml, single neck, round bottom flask 46.4 g of the alkoxylated polyol of Scheme I, Step 1 (0.00898 moles), 70 mls of methanol and 6.96 g of 25 weight percent sodium methoxide solution (in methanol). Concentrate the mixture by evaporating the methanol on a rotary evaporator at 60° C. for one hour followed by Kugelrohr at 60° C. at less than 0.5 mm mercury pressure by gauge. Cool the concentrated solution and dissolve or disperse in 200 ml of THF. Transfer the solution or suspension to a 500 ml flask and add with mechanical stirring under a blanket of argon gas, 4.12 g (0.0539 moles) of allyl chloride. Heat the mixture at 40° C. for 4 hours. Strip the resulting sample of solvent on a rotary evaporator. Anaylysis by NMR of the resulting sample shows 5 of the 6 akoxylated polyol —OH groups substituted with allyl ether groups.

Step 2: Alkylation of the Product of Synthesis II, Step 1

Alkylation processes are known in the art for aryl compounds. These processes applied to the 1,2,3,4-tetrahydroisoquinoline using the allyl capped alkoxylated polyol of Scheme II, step 1. This can also be applied to the N-substituted 1,2,3,4-tetrahydroisoquinoline. It is an option to alkylate isoquinolines directly providing an isoquinoline terminated alkoxylated polyol which is then reduced according to DE 19507522 A1. The resulting 3,4-dihydroisoquinoline terminated alkoxylated polyol can be converted according to WO 03/104199 A2 to the iminium internal salt terminated alkoxylated polyol.

Step 3—optional step of converting the product of Synthesis II, step 2, wherein $R_4$ Of formula (II) is hydrogen, such as 1,2,3,4-tetrahydroisoquinoline terminated alkoxylated polyol, to a tertiary amine of 1, 2,3,4-tetrahydroisoquinoline terminated alkoxylated polyol (i.e., N-substituted 1,2,3,4-tetrahydroisoquinoline terminated alkoxylated polyol) via reaction with alkyl halides as known in the art. Preferably $CH_3Cl$, $CH_3Br$, and mixtures thereof.

Step 4—Oxidation of the product of Synthesis II, step 4 can be performed directly on the N-substituted 1,2,3,4-tetrahydroisoquinoline using the process discussed in Synthesis I, step 4

EXAMPLE 3

Synthesis Scheme III:

Step 1: Preparation of the Glycidal Terminated Alkoxylated Polyol.

Add the product of Synthesis 1, step 1, the alkoxylated polyol (77.5 g, 15 mmol) and stannic chloride (0.6 g, 3 mmol) to a flame dried, 500 ml round bottomed flask equipped with an addition funnel charged with epichlorohydrin (46.86 g, 51 mmol). Keep the reaction under an argon gas atmosphere and warm to 90° C. using an oil bath. Drip epichlorohydrin into the stirring solution over 1 hr., follow by stirring at 90° C. for 18 hours. Add to the cooled reaction mixture tetrahydrofuran (70 mL) and stir the entire mixture, maintaining at a temperature of from about 20° C. to about 25° C. under an argon atmosphere. Add potassium tert-butoxide (5.84 g, 51 mmol) to the stirred solution and stir the suspension at a temperature from about 20° C. to about 25° C. for 18 hours to produce the glycidal ether of the alkoxylated polyol.

Step 2: Preparation of the Cyclic Sulfate Terminated Alkoxylated Polyol

Add sulfur trioxide-dimethylformamide complex ( 2.3 gm, 0.0151 mol.) and toluene (100 ml.) to a flame dried 3 neck round bottomed flask, equipped with an argon inlet, condenser, and a magnetic stir bar. Bring the reaction to reflux, and once at reflux, add 10 g of molten alkoxylated polyol of Synthesis III, step 1 (~0.00425 mol) and reflux the reaction mixture for 45 minutes. Cool the reaction mixture to room temperature (20° C.), dilute with diethyl ether (100 ml) and extract the resulting organic solution with a saturated sodium bicarbonate solution. Separate the organic phase, dry with sodium sulfate, filter, and evaporate the organic filtrate to dryness. The resulting 3-cyclic sulfate terminated alkoxylated polyol can be used without further purification.

Step 3: Conversion of the Product of Synthesis III, Step 2 to the Isoquinolinium Zwitterionic Terminated Diakoxylated Poloyl Via Reaction with 3,4-Dihydroisoquinoline.

Add to the crude cyclic sulfate product of Synthesis III, step 2, diethyl ether, and 3,4-dhydroisoquinoline (3 equivalent based on starting glycidal epoxide containing approximately 3-cyclic sulfate terminated groups per molecule of the polymer) to a 250 mL round bottomed flask. Maintain the reaction at a temperature of from about 20° C. to about 25° C. and stir for 48 hours. Strip the resulting product of ether. Analysis shows the product having at least some conversion to the desired product containing the inner salt as shown in Synthesis III.

EXAMPLE 4

Synthesis Scheme I with some Addition of Propylene Oxide Blocks

Steps 1-4: Addition of Some Propylene Oxide in Molecule for Hydrophobizing the Polymer The reaction procedures are identical to Synthesis I, with the exception that during step 1 of Synthesis I, initially add 60 mole equivalents of propylene oxide, to give hydrophobicity to the polyol, followed by the addition of the same amount of ethylene oxide as in Synthesis I, step 1.

Cleaning Compositions

The present invention further relates to a cleaning composition comprising the modified alkoxylated polyol compound of the present invention. The cleaning compositions can be in any conventional form, namely, in the form of a liquid, powder, granules, agglomerate, paste, tablet, pouches, bar, gel, types delivered in dual-compartment containers, spray or foam detergents, premoistened wipes (i.e., the cleaning composition in combination with a nonwoven material such as that discussed in U.S. Pat. No. 6,121,165, Mackey, et al.), dry wipes (i.e., the cleaning composition in combination with a nonwoven materials, such as that discussed in U.S. Pat. No. 5,980,931, Fowler, et al.) activated with water by a consumer, and other homogeneous or multiphase consumer cleaning product forms.

In addition to cleaning compositions, the compounds of the present invention may be also suitable for use or incorporation into industrial cleaners (i.e. floor cleaners). Often these cleaning compositions will additionally comprise surfactants and other cleaning adjunct ingredients, discussed in more detail below. In one embodiment, the cleaning composition of the present invention is a liquid or solid laundry detergent composition.

In another embodiment, the cleaning composition of the present invention is a hard surface cleaning composition, preferably wherein the hard surface cleaning composition impregnates a nonwoven substrate. As used herein "impregnate" means that the hard surface cleaning composition is placed in contact with a nonwoven substrate such that at least a portion of the nonwoven substrate is penetrated by the hard surface cleaning composition, preferably the hard surface cleaning composition saturates the nonwoven substrate.

In another embodiment the cleaning composition is a liquid dish cleaning composition, such as liquid hand dishwashing compositions, solid automatic dishwashing cleaning compositions, liquid automatic dishwashing cleaning compositions, and tab/unit does forms of automatic dishwashing cleaning compositions.

The cleaning composition may also be utilized in car care compositions, for cleaning various surfaces such as hard wood, tile, ceramic, plastic, leather, metal, glass. This cleaning composition could be also designed to be used in a personal care composition such as shampoo composition, body wash, liquid or solid soap and other cleaning composition in which surfactant comes into contact with free hardness and in all compositions that require hardness tolerant surfactant system, such as oil drilling compositions.

Modified Alkoxylated Polyol Compounds

The cleaning composition of the present invention may comprise from about 0.005% to about 30%, preferably from about 0.01% to about 10%, more preferably from about 0.05% to about 5% by weight of the cleaning composition of a compound as described herein.

Surfactants—The cleaning composition of the present invention may comprise a surfactant or surfactant system comprising surfactants selected from nonionic, anionic, cationic, ampholytic, zwitterionic, semi-polar nonionic surfactants; and other adjuncts such as alkyl alcohols, or mixtures thereof. The cleaning composition of the present invention further comprises from about from about 0.01% to about 90%, preferably from about 0.01% to about 80%, more preferably from about 0.05% to about 50%, most preferably from about 0.05% to about 40% by weight of the cleaning composition of a surfactant system having one or more surfactants.

Anionic Surfactants

Nonlimiting examples of anionic surfactants useful herein include $C_8$-$C_{18}$ alkyl benzene sulfonates (LAS); $C_{10}$-$C_{20}$ primary, branched-chain and random alkyl sulfates (AS); $C_{10}$-$C_{18}$ secondary (2,3) alkyl sulfates; $C_{10}$-$C_{18}$ alkyl alkoxy sulfates ($AE_xS$) wherein preferably x is from 1-30; $C_{10}$-$C_{18}$ alkyl alkoxy carboxylates preferably comprising 1-5 ethoxy units; mid-chain branched alkyl sulfates as discussed in U.S. Pat. No. 6,020,303 and U.S. Pat. No. 6,060,443; mid-chain branched alkyl alkoxy sulfates as discussed in U.S. Pat. No. 6,008,181 and U.S. Pat. No. 6,020,303; modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; methyl ester sulfonate (MES); and alpha-olefin sulfonate (AOS).

Nonionic Surfactants

Non-limiting examples of nonionic surfactants include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates such as PLURONIC® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, $BAE_x$, wherein x 1-30, as discussed in U.S. Pat. No. 6,153,577, U.S. Pat. No. 6,020,303 and U.S. Pat. No. 6,093,856; Alkylpolysaccharides as discussed in U.S. Pat. No. 4,565,647 Llenado, issued Jan. 26, 1986; specifically alkylpolyglycosides as discussed in U.S. Pat. No. 4,483,780 and U.S. Pat. No. 4,483,779; Polyhydroxy fatty acid amides (GS-base) as discussed in U.S. Pat. No. 5,332,528, WO 92/06162, WO 93/19146, WO 93/19038, and WO 94/09099; and ether capped poly(oxyalkylated) alcohol surfactants as discussed in U.S. Pat. No. 6,482,994 and WO 01/42408.

Cationic Surfactants

Non-limiting examples of cationic surfactants include: the quaternary ammonium surfactants, which can have up to 26 carbon atoms, including, but not limited to alkoxylate quaternary ammonium (AQA) surfactants as discussed in U.S. Pat. No. 6,136,769; dimethyl hydroxyethyl quaternary ammonium (K1) discussed in U.S. Pat. No. 6,004,922; polyamine cationic surfactants as discussed in WO 98/35002, WO 98/35003, WO 98/35004, WO 98/35005, and WO 98/35006; cationic ester surfactants as discussed in U.S. Pat. Nos. 4,228, 042, 4,239,660 4,260,529 and U.S. Pat. No. 6,022,844; and amino surfactants as discussed in U.S. Pat. No. 6,221,825 and WO 00/47708, specifically amido propyldimethyl amine.

Cleaning Adjunct Materials

In general, a cleaning adjunct is any material required to transform a cleaning composition containing only the minimum essential ingredients into a cleaning composition useful for laundry, hard surface, personal care, consumer, commercial and/or industrial cleaning purposes. In certain embodiments, cleaning adjuncts are easily recognizable to those of skill in the art as being absolutely characteristic of cleaning products, especially of cleaning products intended for direct use by a consumer in a domestic environment. A comprehensive list of suitable laundry or cleaning adjunct materials can be found in WO 99/05242.

The precise nature of these additional components, and levels of incorporation thereof, will depend on the physical form of the cleaning composition and the nature of the cleaning operation for which it is to be used.

The cleaning adjunct ingredients if used with bleach should have good stability therewith. Certain embodiments of cleaning compositions herein should be boron-free and/or phosphate-free as required by legislation. Levels of cleaning adjuncts are from about 0.00001% to about 99.9%, preferably from about 0.0001% to about 50%, further from about 0.0001 to about 20 wt % by weight of the cleaning compositions. Use levels of the overall cleaning compositions can vary widely depending on the intended application, ranging for example from a few ppm in solution to so-called "direct application" of the neat cleaning composition to the surface to be cleaned.

Common cleaning adjuncts include builders, enzymes, polymers not discussed above, bleaches, bleach activators, catalytic materials and the like excluding any materials already defined hereinabove as part of the essential component of the cleaning compositions of the present invention. Other cleaning adjuncts herein can include suds boosters, suds suppressors (antifoams) and the like, diverse active ingredients or specialized materials such as dispersant polymers (e.g., from BASF Corp. or Rohm & Haas) other than those described above, color speckles, silvercare, anti-tarnish and/or anti-corrosion agents, dyes, fillers, germicides, alkalinity sources, hydrotropes, anti-oxidants, enzyme stabilizing agents, pro-perfumes, perfumes, solubilizing agents, carriers, processing aids, pigments, and, for liquid formulations, solvents, chelating agents, dye transfer inhibiting agents, dispersants, brighteners, suds suppressors, dyes, structure elasticizing agents, fabric softeners, anti-abrasion agents, hydrotropes, processing aids, and other fabric care agents, surface and skin care agents. Suitable examples of such other cleaning adjuncts and levels of use are found in U.S. Pat. Nos. 5,576,282, 6,306,812 B1 and 6,326,348 B1.

METHOD OF USE

The present invention includes a method for cleaning a surface or fabric. Such method includes the steps of contacting a modified alkoxylated polyol compound of the present invention or an embodiment of the cleaning composition comprising the modified alkoxylated polyol compound of the present invention, in neat form or diluted in a wash liquor, with at least a portion of a surface or fabric then optionally rinsing such surface or fabric. Preferably the surface or fabric is subjected to a washing step prior to the aforementioned optional rinsing step. For purposes of the present invention, washing includes but is not limited to, scrubbing, and mechanical agitation.

As will be appreciated by one skilled in the art, the cleaning compositions of the present invention are ideally suited for use in home care (hard surface cleaning compositions), personal care and/or laundry applications. Accordingly, the present invention includes a method for cleaning a surface and/or laundering a fabric. The method comprises the steps of contacting a surface and/or fabric to be cleaned/laundered with the modified alkoxylated polyol compound or a cleaning composition comprising the modified alkoxylated polyol compound. The surface may comprise most any hard surface being found in a typical home such as hard wood, tile, ceramic, plastic, leather, metal, glass, or may consist of cleaning surfaces in a personal care product such as hair and skin. The surface may also include dishes, glasses, and other cooking surfaces. The fabric may comprise most any fabric capable of being laundered in normal consumer use conditions.

The cleaning composition solution pH is chosen to be the most complimentary to a surface to be cleaned spanning broad range of pH, from about 5 to about 11. For personal care such as skin and hair cleaning pH of such composition preferably has a pH from about 5 to about 8 for laundry cleaning compositions pH of from about 8 to about 10. The compositions are preferably employed at concentrations of from about 200 ppm to about 10,000 ppm in solution. The water temperatures preferably range from about 5° C. to about 100° C.

For use in laundry cleaning compositions, the compositions are preferably employed at concentrations from about 200 ppm to about 10000 ppm in solution (or wash liquor). The water temperatures preferably range from about 5° C. to about 60° C. The water to fabric ratio is preferably from about 1:1 to about 20:1.

The present invention included a method for cleaning a surface or fabric. Such method includes the step of contacting a nonwoven substrate impregnated with an embodiment of the cleaning composition of the present invention, and contacting the nonwoven substrate with at least a portion of a surface and/or fabric. The method may further comprise a washing step. For purposes of the present invention, washing includes but is not limited to, scrubbing, and mechanical agitation. The method may further comprise a rinsing step.

As used herein "nonwoven substrate" can comprise any conventionally fashioned nonwoven sheet or web having suitable basis weight, caliper (thickness), absorbency and strength characteristics. Examples of suitable commercially available nonwoven substrates include those marketed under the tradename SONTARA® by DuPont and POLYWEB® by James River Corp.

As will be appreciated by one skilled in the art, the cleaning compositions of the present invention are ideally suited for use in hard surface applications. Accordingly, the present invention includes a method for cleaning hard surfaces comprising the steps of contacting a hard surface to be cleaned with the cleaning composition or solution thereof or nonwoven substrate impregnated with an embodiment of the cleaning composition of the present invention. The method of use comprises the steps of contacting the cleaning composition with at least a portion of the nonwoven substrate, then contacting a hard surface by the hand of a user or by the use of an implement to which the nonwoven substrate attaches.

As will be appreciated by one skilled in the art, the cleaning compositions of the present invention are ideally suited for use in liquid dish cleaning compositions. The method for using a liquid dish composition of the present invention comprises the steps of contacting soiled dishes with an effective amount, typically from about 0.5 ml. to about 20 ml. (per 25 dishes being treated), preferably from about 3 ml. to about 10 ml., of the liquid dish cleaning composition of the present invention diluted in from about 2000 ml. to about 20000 ml., water.

The soiled dishes are immersed in the sink containing the diluted compositions then obtained, where contacting the soiled surface of the dish with a cloth, sponge, or similar article cleans them. The cloth, sponge, or similar article may be immersed in the cleaning composition and water mixture prior to being contacted with the dish surface or the cleaning composition may be applied directly to the cloth, sponge, or similar article without being diluted in the water, and is typically contacted with the dish surface for a period of time ranged from about 1 to about 10 seconds, although the actual time will vary with each application and user. The contacting of cloth, sponge, or similar article to the dish surface is preferably accompanied by a concurrent scrubbing of the dish surface.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A bleach activating compound comprising a polyol source, the polyol source comprising at least two hydroxy moieties, at least one of the hydroxy moieties further comprising an alkoxy moiety, the alkoxy moiety is selected from the group consisting of ethoxy, propoxy, butoxy and mixtures thereof; further wherein at least one of the hydroxy moieties further comprise a bleach activating unit having formula (IV):

(IV)

wherein $R_1$ of formula (IV) is independently selected from the group consisting of the polyol source, a $C_6$-$C_{20}$ substituted or unsubstituted aryl; a $C_2$-$C_{20}$ substituted or unsubstituted heteroaryl group, and mixtures thereof; $R_2$ of formula (IV) is independently selected from the group consisting of the polyol source, a $C_1$-$C_{20}$ substituted or unsubstituted alkyl; $C_2$-$C_{20}$ substituted or unsubstituted alkenyl, and mixtures thereof; $R_3$ of formula (IV) is independently selected from the group consisting of the polyol source, hydrogen, a $C_1$-$C_{20}$ substituted or unsubstituted alkyl, $C_2$-$C_{20}$ substituted or unsubstituted alkenyl, a $C_6$-$C_{20}$ substituted or unsubstituted aryl; a $C_2$-$C_{20}$ substituted or unsubstituted heteroaryl moiety and mixtures thereof; $R_4$ of formula (IV) is independently selected from the group consisting of the polyol source, a $C_1$-$C_{20}$ substituted or unsubstituted alkyl, a $C_6$-$C_{20}$ substituted or unsubstituted aryl, a $C_2$-$C_{20}$ substituted or unsubstituted heteroaryl group, and mixtures thereof; such that at least one ring structure results from a selection of two moieties from the group of $R_1$, $R_2$, $R_3$ and $R_4$ of formula (IV) in combination with the oxaziridinium bond; in that the two moieties from the group of $R_1$, $R_2$, $R_3$ and $R_4$ of formula (IV) selected to form the ring structure do not comprise the polyol source.

2. The compound of claim 1 wherein at least one $R_1$, $R_2$, $R_3$ and $R_4$ of formula (IV) is selected as a $C_6$-$C_{20}$ substituted or unsubstituted aryl.

3. The compound of claim 1 wherein the hydroxy moieties comprise the alkoxy moiety comprising an average degree of alkoxylation per hydroxy moiety from about 0.1 to about 200.

4. The compound of claim 3 wherein the polyol source comprises an average degree of alkoxylation per hydroxy moiety from about 1 to about 200 to form an alkoxy moiety and the alkoxy moiety terminates in the bleach activating unit of formula (IV).

5. The compound of claim 1 wherein the polyol source is derived from a sugar or reduced sugar monomers being selected from the group of: glucose, maltose, maltotriose, maltopentose, maltohexose sorbitol, maltitol, sucrose, xylitol, glycerol, glycerol derivatives, polyglycerol, pentaerythitol, polyethylene glycol, polypropylene glycol, poly vinyl alcohol, xylan, reduced maltotriose, reduced maltodextrins, and mixtures thereof.

6. A cleaning composition comprising the bleach activating compound according to claim 1.

7. The cleaning composition of claim 6 wherein the cleaning composition further comprises a surfactant selected from anionic, nonionic, cationic, zwitterionic, amphoteric, and mixtures thereof.

8. A cleaning composition comprising:
    from 0.005% to about 30% of the bleach activating compound according to claim 1.

* * * * *